Figure 1:
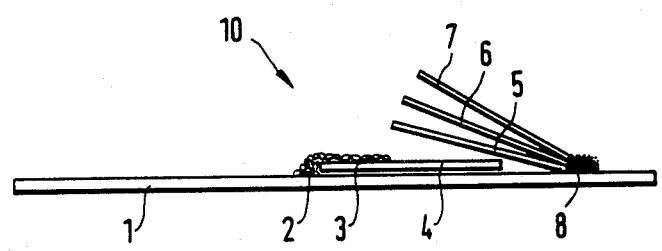

United States Patent [19]

Bartl et al.

[11] Patent Number: 4,861,712
[45] Date of Patent: Aug. 29, 1989

[54] ANALYSIS ELEMENT FOR DETERMINATION OF A COAGULATION PARAMETER

[75] Inventors: Knut Bartl, Wilzhofen; Helmut Lill, Wielenbach; Hans Wielinger, Weinheim, all of Fed. Rep. of Germany

[73] Assignee: Boehringer Manneheim GmbH, Mannheim, Fed. Rep. of Germany

[21] Appl. No.: 46,659

[22] Filed: May 4, 1987

[30] Foreign Application Priority Data

May 16, 1986 [DE] Fed. Rep. of Germany ....... 3616496

[51] Int. Cl.[4] ...................... C12Q 1/56; G01N 33/86; G01N 1/48
[52] U.S. Cl. ...................... 435/13; 435/177; 435/176; 435/805; 436/69; 436/169; 436/170; 436/810; 422/56; 422/57; 422/58; 422/101
[58] Field of Search ................ 435/13, 23.4, 212, 214, 435/217, 176, 177, 805; 436/69, 169, 170, 810; 422/58, 56, 57, 101

[56] References Cited

U.S. PATENT DOCUMENTS

| 4,473,639 | 9/1984 | Sommer et al. ...................... 435/13 |
| 4,477,575 | 10/1984 | Vogel et al. ...................... 422/56 X |
| 4,557,901 | 12/1985 | Koyama et al. ...................... 422/56 |
| 4,610,962 | 9/1986 | Takagi et al. ...................... 435/177 X |

FOREIGN PATENT DOCUMENTS

| 0014039 | 6/1980 | European Pat. Off. .............. 435/13 |
| 0162302 | 10/1985 | European Pat. Off. .............. 422/56 |
| 0194578 | 9/1986 | European Pat. Off. ............... 435/4 |
| 3540526 | 5/1987 | Fed. Rep. of Germany .......... 435/4 |
| 0237326 | 9/1986 | German Democratic Rep. .... 435/4 |

OTHER PUBLICATIONS

Chemical Abstract 104: 31351.
Chemical Abstract 105: 94109.
Palmer et al., Blood 59(1): 38–42 (1982).
Ogston et al., Brit. Med. Bull. 34(2): 107–112 (1978).

Primary Examiner—Esther M. Kepplinger
Assistant Examiner—Carol A. Spiegel
Attorney, Agent, or Firm—Felfe & Lynch

[57] ABSTRACT

The present invention provides an analysis element for the determination of coagulation parameters with the help of a detectable or a detection reaction-initiating substrate of a protease of the blood coagulation system and at least one factor and/or co-factor of the blood coagulation system and a buffer substance, wherein the factor and/or co-factor, together with a water-soluble, non-ionic polymer which does not falsely influence the course of the coagulation cascade, is impregnated on an open, planar composite structure which consists of a material which does not have a disturbing influence on the course of the coagulation.

22 Claims, 1 Drawing Sheet

ANALYSIS ELEMENT FOR DETERMINATION OF A COAGULATION PARAMETER

The present invention is concerned with an analysis element for the determination of coagulation parameters with the help of a detectable or a detection reaction-initiating substrate of a protease of the blood coagulation system and at least one factor and/or co-factor of the blood coagulation system and a buffer substance.

Such as analysis element is described in the older U.S. patent application Ser. No. 798,955 and reference is made to the complete contents of this Application. A carrier material, preferably paper or a fleece, is there employed. In another embodimental form of the there-described analysis element, the substrate and/or the co-factor is present in a water-soluble, film-forming polymer. The reagent-containing film is applied to a base foil.

If, with the analysis element described in the above-mentioned earlier U.S. patent application, it is desired to determine, for example, the one-phase coagulation time according to Quick, then it contains thromboplastin as co-factor (sometimes also called activator), calcium ions and a substrate for thrombin (a protease of the blood coagulation system). If this analysis element is brought into contact with plasma by applying, for example, a drop of plasma thereto, then the coagulation cascade is started by the presence of the thromboplastin and of the calcium ions. The thrombin arising in the course of the coagulation cascade splits the substrate. The substrate is so chosen that, after the splitting, it is either directly detectable or initiates a detection reaction. In general, a colour formation is used. In this case, the substrate is either itself colour-forming or the fission product indirectly initiates a colour formation via a subsequent reaction. Alternatively, for the detection reactions there can also be used, for example, substrates which produce fluorescing coloured materials. For the present invention, the type of the detection reaction is immaterial.

The process described in the above-mentioned earlier U.S. patent application signifies a considerable advance because, for the first time, an analysis element (which sometimes is also called a dry test or test carrier) is provided for the determination of parameters of the blood coagulation system. However, it leaves something to be desired with regard to the precision of the measurement results obtained. In the scope of the present invention, it was recognised that the papers or fleeces usually employed for analysis elements so influence the course of the coagulation cascade in many cases that the measurement result does not achieve the degree of exactitude desirable from a medical point of view.

If the reagents are incorporated into a water-soluble film, then, in the case of appropriate choice of the film former, an influencing of the coagulation cascade in the above-mentioned sense is admittedly avoided. Nevertheless, the precision of the measurement leaves something to be desired. As was also recognised in the scope of the present invention, this can be attributed to the fact that the film layer liberates the reagents comparatively slowly. However, for a coagulation test, the reagents must be liberated as quickly as possible because the coagulation properties of the sample are determined via a time measurement. The starting point of this period of time becomes imprecise due to a delayed liberation of the reagents.

Therefore, it is an object of the present invention to provide an analysis element for coagulation tests which is just as easy to handle as that described in the above-mentioned earlier U.S. patent application but has an improved precision.

It is an object of the present invention to provide a process for the determination of coagulation parameters comprising separating a plasma component of a blood sample, contacting said plasma component with an analysis element as described below, and a detectable or detection reaction initiating substrate of a protease of the blood coagulation system.

Thus, according to the present invention, there is provided an analysis element for the determination of coagulation parameters with the help of a detectable or a detection reaction-initiating substrate of a protease of the blood coagulation system and at least one factor and/or co-factor of the blood coagulation system and a buffer substance, wherein the factor and/or co-factor, together with a water-soluble, non-ionic polymer which does not falsely influence the course of the coagulation cascade, is impregnated on an open, planar composite structure which consists of a material which does not have a disturbing influence on the course of the coagulation cascade.

The open planar composite structure is to be understood to be any structure which is planar extended, i.e. it has a small thickness (preferably less than 0.5 mm. and especially preferably less than 0.25 mm.) The area of the device is determined by how large a test field is desired. By "open" there is meant that the structure is capable of enabling a rapid penetration of an aqueous liquid, for example a plasma sample, the structure having the largest possible surface which can be brought into contact with the sample. There would be suitable, for example, a sieve-like structure of a synthetic resin material, i.e. a synthetic resin foil with very many holes arranged close together. However, especially preferred is a fabric, a textile or a mesh which consists of filaments, monofilaments being especially suitable.

The material for producing the planar composite structure can, in principle, be any material which has no disturbing influence on the course of the coagulation cascade and from which, production technically, a structure of the described kind can be produced. Furthermore, the material must be such that the non-ionic polymer adheres with the reagents thereon. Especially preferred materials are polyamides, polyesters and mixed fabrics of these fibres. The filament number per cm. is preferably greater than 20.

The question whether the material selected for the composite structure influences the course of the extrinsic coagulation cascade can be tested as follows: 40 mg. of the material are incubated with 300 $\mu$l. of citrate plasma for 60 seconds at 37° C. Thereafter, the plasma is centrifuged off and the coagulatability of the plasma must not have changed statistically significantly.

The non-ionic polymer must have the property that, in the case of the use of usual temperatures, it dissolves sufficiently quickly in the aqueous medium. We have found that even materials which, in the case of greater layer thickness, only dissolved in water sufficiently quickly at temperatures above ambient temperature can also be used because they are present in a thin layer on the composite structure according to the present invention.

Furthermore, the non-ionic polymer must have the property of forming an adherent, thin layer on the planar composite structure. In contradistinction to a coating such as is usual, for example in the production of rain-repellent clothing in which a polymer material is applied to a fabric layer in such a manner that the polymer layer remains substantially on one side of the fabric structure and bridges over its openings, the composite structure according to the present invention is impregnated with the non-ionic polymer, i.e. the polymer covers the composite structure on all sides.

Examples of polymers which can be used include non-ionic cellulose derivatives, polyvinylpyrrolidones and polyxanthanes.

Polyethylene oxides, polyacrylamides, as well as polyvinyl acetates saponified partly or completely in polyvinyl alcohol, have proved to be especially useful. Within the last-mentioned group of materials, partly saponified polyvinyl acetates are preferred. Especially preferred are polyvinyl acetates with a degree of saponification of from 70 to 93 mole %. Surprisingly, all these polymers have the additional advantage that they stabilise thromboplastin. In this way, a Quick test can be produced which has an especially good storage behaviour.

Mixtures of appropriate non-ionic polymers can possibly also be used.

For the production of the reagent carrier according to the present invention, there is first prepared a solution of the factor and/or of the co-factor and of the non-ionic water-soluble polymer. Other components, for example plasticisers, can possibly also be added. The planar composite structure is impregnated with this solution preferably by dipping in but, under certain circumstances, also by spraying. The appropriate viscosity of the impregnation solution cannot be generally ascertained but rather is to be determined for every non-ionic polymer or polymer mixture under production-technical conditions on the fabric in question. Viscosities of from 50 to 250 mPa sec. have proved to be useful.

The substrate acting as indicator can be impregnated on to the planar composite structure, together with the factor and/or co-factor and the non-ionic, water-soluble polymer. However, under certain circumstances, problems can arise in using the factor and/or co-factor together with the substrate. In this case, it has proved to be preferable to apply the substrate to a separate carrier material. For this purpose, various known carrier materials can be used. However, in this case, too, it is especially preferred to use an open, planar composite structure as carrier material, which is impregnated, analogously to the above-described process, with a solution which, besides the substrate, contains a non-ionic, water-soluble polymer. There is thus obtained an especially uniform dissolving behaviour of both carrier material layers which, on the one hand, contain the factor and/or co-factor and, on the other hand, the substrate serving as indicator.

According to another preferred embodiment of the present invention, the open, planar composite structure or, when more than one such structure is used, at least one thereof is impregnated with the calcium ions which, in coagulation tests, are generally necessary for the recalcifying of the plasma.

Buffer substances can also be impregnated together with the factor and/or co-factor but they can also be present on a separate carrier material of the analysis element.

The present invention will now be described in more detail in the following, with reference to the accompanying drawing and to specific examples.

FIG. 1 of the accompanying drawing shows an analysis element according to the present invention schematically in cross-section.

Referring to the accompanying drawing, a carrier foil 1 as carrying component of the analysis element is indicated generally with 10. In the illustrated embodiment, it has a longitudinal form as in the case of a test strip. However, the present invention can also be used for other forms of analysis elements which have, for example, a quadratic form similar to photographic slides or prints.

On the carrier foil, an erythrocyte separating and plasma transport fleece is fixed with a melt adhesive 2. It is especially preferred to use a fleece of coagulation-neutral glass fibre material, such as is described in U.S. patent application Ser. Nos. 021,743 and 027,628. The fleece 4, in the following briefly referred to as transport fleece, is partly covered with a covering mesh 3 also fixed with the adhesive 2, a nylon mesh being appropriate for this purpose.

Three further planar-shaped components of the analysis element 10 are fixed on to the carrier foil 1 with a strip of melt adhesive in such a manner that they partly overlap the transport fleece 4. Since they are only fixed on one of their edges with one another and to the carrier foil 1, over their remaining surface they have a distance from one another so long as they are not pressed on to one another by external pressure. More details of this kind of test construction are to be found, for example, in published European patent application No. 0,045,476.

As lowermost layer, there is provided an oxidising agent carrier 5 which, in the following, is also referred to as oxidation matrix, above it is provided a reagent carrier 6 according to the present invention in the form of an impregnated open composite structure and, as uppermost layer, there is provided a covering foil 7.

For the layer 6, there is preferably used a fabric which is impregnated with a solution in which the film former, buffer, thromboplastin or other start reagent for the start of the extrinsic or intrinsic coagulation cascade, as well as the indicator, a substrate for a protease arising in the course of the blood coagulation, for example Factor IIa, Factor Xa or the like, and possibly also a coupler, as well as calcium ions and possibly also a plasticiser for the film former, are dissolved in water. As buffer substances, there have proved useful Tris and compounds from the Good buffer series. As substrates, there can be used all protease substrates which, on the basis of their amino acid sequence, are sufficiently specific, for example Tos-Gly-Pro-Arg-4-nitroanilide acetate or Tos-Gly-Pro-Arg-p-pentylenediamine acetate, and N-methylanthranilic acid as coupler. Other couplers, such as N-(4-fluorophenyl)-N-methylaminomethane phosphonic acid and the like, can also be used.

In the case of indicators which, after splitting by the protease, give a colour via a connected oxidative coupling, it is necessary to provide an oxidation agent, for example potassium hexacyanoferrat-III, in the layer 5. Calcium ions can possibly also be present in the layer 5. For the layer 5, there is preferably also used a thin fabric which has been impregnated. Insofar as an indicator is used in which a strengthening reaction via an oxidative coupling is not necessary, the via an oxidative coupling is not necessary, the oxidation matrix 5 is omitted.

In the case of the above-mentioned alternative embodiment with separate storage of the substrate the layer 5 can also be a planar composite structure, on which the substrate is impregnated separated from the factor and/or the cofactor.

More details regarding the chemical composition of various coagulation tests which can also be used for the present invention are given in the initially mentioned U.S. patent application Ser. No. 798,955.

In the following Examples, the results such as are achieved with reagent films on foils according to the above-mentioned U.S. patent application are compared with results obtained with fabrics impregnated according to the invention:

Production of an analysis element for the determination of the one-phase coagulation time according to Quick.
Production of reagent films (reagent matrix) on foil.

On to polycarbonate foils with a thickness of 200 μm. are raked on, with a wet film thickness of 100 μm., films of the compositions set out in the following Table 1 and dried at 45° C. After the drying, the coated foil strips are cut up into a breadth of 15 mm.

Production of impregnated fabrics (according to the present invention).

Polyamide fabrics (Type 75 Hc of the firm Züricher Beuteltuchfabrik, Switzerland) are impregnated with impregnation solutions of the compositions given in the following Table and dried at 45° C. After the drying, the impregnated fabric strips are cut up into a breadth of 15 mm.

Production of the oxidation matrix.

A nylon mesh (Type NY 20 Hc Super of the firm Züricher Beuteltuchfabrik, Switzerland) is impregnated with an aqueous solution of 50 mmole/liter of potassium hexacyanoferrat-III, 50 mmole/liter calcium chloride and 0.2 g./liter polyacrylamide (ROHAGIT 700 of the firm Röhm) and dried at 45° C. After the drying, strips of 15 mm. breadth are cut from the impregnated mesh.

Production of the coating and impregnation masses.

In 1 liter of distilled water are dissolved 100 mMole Hepes, 1 mMole Tos-Gly-Pro-Arg-p-phenylenediamine, 15 mMole N-(4-fluorphenyl)-N-methylaminomethanephosphoric acid, 2.5 g. thromboplastin and the polymers given in Table 1. These solutions are adjusted to a pH of 7.5 with aqueous sodium hydroxide solution.

TABLE 1

| polymer | amount in the coating mass | amount in the impregnation solution |
| --- | --- | --- |
| 1. polyvinyl alcohol (MOWIOL 26/88, Hoechst) | 70 g | 40 g. |
| 2. polyvinyl alcohol (MOWIOL 18/88, Hoechst) | 75 g. | 50 g. |
| 3. polyethylene oxide (POLYOX 301, Union Carbide) | 10 g. | 1 g. |
| polyacrylamide (ROHAGIT 700 Rohm) | 5 g. | 2.5 g. |
| 4. polyvinyl alcohol (MOWIOL 18/88, Hoechst) | 60 g. | 40 g. |
| polyacrylamide (ROHAGIT 700, Rohm) | 10 g. | 5 g. |

Production of the analysis element.

On to a 100 mm. wide polystyrene foil (1 in FIG. 1) is laid a glass fibre fleece (4 in FIG. 1) according to German patent application No. 35 23 969 with a weight per unit surface area of 30 to 40 g./m² in a breadth of 15 mm., partly covered with a nylon mesh (3 in FIG. 1) and fixed on one end with an adhesive (2 in FIG. 1). On the free end of the glass fibre fleece are placed above one another the oxidation matrix (5 in FIG. 1) and reagent matrix (6 in FIG. 1) and covered with a 200 μm. thick transparent polycarbonate foil (7 in FIG. 1) of 15 mm. breadth and firmly fixed with an adhesive 8 (2 in FIG. 1). The so produced bands are cut up into 6 mm. wide strips.

The construction of the analysis element with a reagent film on foil corresponds essentially to the described construction according to FIG. 1. However, it differs in that, instead of the layers 6 and 7, there is provided a single layer. This consists of a transparent foil which is coated with the film. It is so arranged that the foil in the FIGURE faces upwardly.

Comparison of the precisions to be achieved with film coating on foil and with the present invention in the determination of the one-phase coagulation time according to Quick.

For this purpose, the following procedure is used:

On to the above-described test strips are pipetted 32 μl. of pool plasma with a Quick value of 100% and a plasma of 12.5% prepared by dilution with physiological sodium chloride solution. The reagent carrier provided with the plasma samples is measured in a REFLOTRON remission photometer (Boehringer Mannheim GmbH). The time is measured which elapses until a remission decrease of 10% has taken place, i.e. the time until the extrinsic coagulation cascade has proceeded to such an extent that a definite amount of thrombin (Factor IIa) has formed.

In the case of the measurement series, in each case, 25 determinations are carried out per test variant and % Quick.

The measurement results obtained are given in the following Table 2.

The four lines of the Table refer to the four different polymers or polymer mixtures of Table 1. In the first two columns are given the measurement results for the film on foil used for comparison. The last two columns show the measurement results for the embodiment according to the present invention.

For each of the embodiments, there are given the measured times for the 100% plasma and for the 12.5% plasma. Important for the assessment of the present invention are especially the also given variation coefficients (VC) in percent.

The measurement results given in Table 2 clearly show that the embodiment according to the present invention gives statistically significant better variation coefficients. In the region of low Quick percentages, in the important therapeutic range, the improved precision appears especially clearly.

TABLE 2

| | film coating | | | | embodiment according to the present invention | | | |
| --- | --- | --- | --- | --- | --- | --- | --- | --- |
| | 100% Quick | | 12.5% Quick | | 100% Quick | | 12.5% Quick | |
| poly-mer | sec. | VC in % | sec. | VC in % | sec. | VC in % | sec. | VC in % |
| 1 | 42.4 | 3.4 | 118.0 | 9.4 | 41.6 | 2.6 | 66.1 | 3.1 |
| 2 | 42.9 | 2.1 | 123.2 | 10.3 | 39.6 | 1.4 | 67.3 | 3.2 |
| 3 | 44.2 | 4.9 | 83.2 | 5.2 | 35.1 | 1.7 | 83.3 | 2.3 |
| 4 | 44.9 | 4.1 | 110.7 | 7.1 | 38.1 | 1.5 | 70.2 | 2.2 |

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Filamentous structure useful for determining a coagulation parameter consisting of filamentous material which neither activates nor inactivates a coagulation cascade system, at least one factor or co-factor of said coagulation cascade system coated onto said filamentous material and a water soluble non-ionic polymer which coats and impregnates said filamentous material, said polymer not falsely influencing said coagulation cascade system.

2. Filamentous structure useful for determining a coagulation parameter consisting of filamentous material which neither activates nor inactivates a coagulation cascade system, at least one factor or co-factor of said coagulation cascade system coated onto said filamentous material, a detectable substrate or detection reaction initiating substrate for said coagulation system coated onto said filamentous material and a water soluble, non-ionic polymer which coats and impregnates said filamentous material, said polymer not falsely influencing said coagulation cascade system.

3. Filamentous structure useful for determining a coagulation parameter consisting of filamentous material which neither activates nor inactivates a coagulation cascade system, at least one factor and at least one co-factor of said coagulation cascade system coated onto said filamentous material and a water soluble non-ionic polymer which coats and impregnates said filamentous material, said polymer not falsely influencing said coagulation cascade system.

4. Filamentous structure of claim 1, wherein said structure is less than 0.5 mm in thickness.

5. Filamentous structure of claim 1 wherein said structure is less than 0.25 mm in thickness.

6. Filamentous structure of claim 1, wherein said material is a filamentous fabric, textile, or mesh.

7. Filamentous structure of claim 1, wherein said material is monofilamentous fabric, monofilamentous textile, or monofilamentous mesh.

8. Filamentous structure of claim 1, wherein said material is polyamide, polyester, or a mixture of polyamide and polyester.

9. Filamentous structure of claim 6, wherein said material has more than 20 filaments per centimeter.

10. Filamentous structure of claim 1, wherein said water soluble non-ionic polymer is a non-ionic cellulose derivative, a polyvinyl pyrrolidone, a polyxanthane, a polyethylene oxide, a polyacrylamide or a partially saponified polyvinyl alcohol.

11. Filamentous structure of claim 10, wherein said water soluble non-ionic polymer is a partially saponified polyvinyl alcohol.

12. Filamentous structure of claim 11, wherein said polyvinyl alcohol saponification ranges from 70 to 93 mole percent.

13. Filamentous structure according to claim 1, wherein the water soluble non-ionic polymer is a film former which is soluble in water at a temperature below 50° C.

14. Filamentous structure according to claim 1, wherein the co-factor is thromboplastin and the water soluble non-ionic polymer is a thromboplasmin stabilizer.

15. Filamentous structure useful for determining a coagulation parameter consisting of filamentous material which neither activates or inactivates a coagulation cascade system, at least one factor or co-factor of said coagulation cascade system coated onto said filamentous material, calcium ions coated onto said filamentous material, and a water soluble non-ionic polymer which coats and impregnates said filamentous material, said polymer not falsely influencing said coagulation cascade system.

16. Filamentous structure useful for determining a coagulation parameter consisting of filamentous material which neither activates or inactivates a coagulation cascade system, at least one factor or co-factor of said coagulation cascade system coated onto said filamentous material, a buffer substance, and a water soluble, non-ionic polymer which coats and impregnates said filamentous material, said polymer not falsely influencing said coagulation cascade system.

17. Filamentous structure useful for determining a coagulation parameter consisting of filamentous material which neither activates nor inactivates a coagulation cascade system, at least one factor or co-factor of said coagulation cascade system coated onto said filamentous material, a detectable substrate or detection reaction initiating substrate for said coagulation cascade system coated onto said filamentous material, a buffer substance and a water soluble, non-ionic polymer which coats and impregnates said filamentous material, said polymer not falsely influencing said coagulation cascade system.

18. Analysis element useful for determining a coagulation parameter comprising a first filamentous structure which neither activates nor inactivates a coagulation cascade system, at least one factor or co-factor of said coagulation cascade system coated onto said first filamentous material and a water soluble, non-ionic polymer which coats and impregnates the filamentous material of said first filamentous structure, said water soluble non-ionic polymer not falsely influencing said coagulation cascade system, and a second filamentous structure consisting of filamentous material which neither activates nor inactivates a coagulation cascade system, a detectable substrate or a detection reaction initiating substrate of said coagulation system coated on said second filamentous structure and a water soluble, non-ionic polymer which coats and impregnates the filamentous material of said second filamentous structure, said water soluble non-ionic polymer not falsely influencing said coagulation cascade system, wherein said first filamentous structure and said second filamentous structure are separate from each other.

19. Analysis element useful for determining a coagulation parameter comprising a first filamentous structure consisting of filamentous material which neither activates nor inactivates a coagulation cascade system, at least one factor or co-factor of said coagulation cascade system coated onto said first filamentous material, a buffer substance and a a water soluble, non-ionic polymer which coats and impregnates the filamentous material of said first filamentous structure, said water soluble non-ionic polymer not falsely influencing said coagulation cascade system, and a second filamentous structure consisting of filamentous material which neither activates nor inactivates a coagulation cascade system, a detectable substrate or a detection reaction initiating substrate of said coagulation system coated on said second filamentous structure and a water soluble, non-ionic polymer which coats and impregnates the filamentous material of said second filamentous structure, said water soluble non-ionic polymer not falsely influencing said coagulation cascade system, wherein said first filamentous structure and said second filamentous structure are separate from each other.

20. Method for determining a coagulation parameter comprising contacting plasma with a filamentous structure of claim 1, adding a detectable substrate or detection reaction indicating substrate for said coagulation cascade system thereto and determining said detectable substrate or detection reaction as a measure of said coagulation parameter.

21. Method for determining a coagulation parameter comprising contacting plasma with a filamentous structure of claim 2 and determining said detectable substrate or detection reaction as a measure of said coagulation parameter.

22. Method for determining a coagulation parameter comprising contacting plasma with the analysis element of claim 18, bring said first filamentous structure and said second filamentous structure into contact with each other and with said plasma and determining said detectable substrate or said detection reaction as an indication of said coagulation parameter.

* * * * *